(12) United States Patent
Tseng et al.

(10) Patent No.: US 7,229,538 B2
(45) Date of Patent: Jun. 12, 2007

(54) MICROFLUIDIC DEVICE WITH NETWORK MICRO CHANNELS

(76) Inventors: Fan-Gang Tseng, No. 100-4, Jianjung Rd., Hsinchu (TW) 300; Kuang-Hua Lin, 12Fl. No. 62, TungDe 7th St., Taoyuan City, Taoyuan (TW) 300; Hui-Ting Hsu, No. 389, Jinding Rd., Sanmin District, Kaohsiung City (TW) 807

( * ) Notice: Subject to any disclaimer, the term of this patent is extended or adjusted under 35 U.S.C. 154(b) by 852 days.

(21) Appl. No.: 10/661,750

(22) Filed: Sep. 11, 2003

(65) Prior Publication Data

US 2004/0050705 A1 Mar. 18, 2004

(30) Foreign Application Priority Data

Sep. 17, 2002 (TW) .............................. 91121297 A

(51) Int. Cl.
*G01N 27/327* (2006.01)
*G01N 27/333* (2006.01)
*B01L 3/00* (2006.01)

(52) U.S. Cl. .................... 204/403.14; 204/403.01; 204/416; 204/409; 422/99; 422/100

(58) Field of Classification Search ............................... 204/403.01–403.15, 416–418, 409–412; 422/99, 100, 101
See application file for complete search history.

(56) References Cited

U.S. PATENT DOCUMENTS

| 6,638,404 | B2* | 10/2003 | Terashima et al. | 204/416 |
| 6,709,559 | B2* | 3/2004 | Sundberg et al. | 204/604 |
| 6,974,526 | B2* | 12/2005 | Lee et al. | 204/451 |
| 2003/0003026 | A1* | 1/2003 | Parce et al. | 422/100 |
| 2003/0215753 | A1 | 11/2003 | Tseng et al. | |

* cited by examiner

*Primary Examiner*—Alex Noguerola
(74) *Attorney, Agent, or Firm*—Egbert Law Offices

(57) ABSTRACT

A microfluidic device has a plurality of H-shaped micro channels not connected to each other and formed on a substrate. Each of the H-shaped micro channels comprises two main channels separately placed on two opposite sides in parallel and a plurality of sub-channels perpendicularly connected to the two main channels. The present invention is designed in such a way that various reagents dropped into different H-shaped micro channels are immobilized on respective sub-channels because of the different widths of the main channel and sub-channel. Afterwards the reagents are coated with a layer of polymer. The polymer has a porous structure that allows the passage of any sample to be tested. Finally, a plurality of upper channels parallel to one another are directly fabricated in the polymer, or in another layer of polymer stacked on the previous polymer.

19 Claims, 7 Drawing Sheets

MICROFLUIDIC DEVICE WITH NETWORK MICRO CHANNELS

BACKGROUND OF THE INVENTION

1. Field of the Invention

The present invention relates to a microfluidic device with network micro channels, and more particularly, to a microfluidic device applicable to biomedical analyses.

2. Description of the Related Art

Microfluidic devices integrated with biochips are getting more and more popular lately, because they provide better operational ways for biological or medical syntheses and analyses. Microfluidic devices are characterized by small size and an automatic diversion function, thus they have plenty of advantages, namely fewer amounts of reagents, miniaturization, fast sensing response, good integration, etc. They minimize manual operations, save reagents and rapidly process voluminous biological data transmitted in parallel, compared with conventional biomedical analytical methods.

By a microfluidic device, it means infusing microliters, or even nanoliters, of liquid into a substrate with micro channels, and making the liquid undergo an intended reaction inside the micro channels by means of a mechanical or non-mechanical pump. To build this miniature structure, it requires a micro electromechanical fabrication method, that is, a fabrication process that involves performing thin film growth, photolithography and etching on a substrate repeatedly. Instead of being limited to a silicon wafer, the substrate can also be glass, quartz or polymer. Polymers from which the substrate can be made include PMMA (polymethylmethacrylate), PC (polycarbonate), PDMS (polydimethylsiloxane), etc.

In U.S. patent application Ser. No. 10/438,527, entitled "Fabrication Method of Three-Dimensional Micro Structures" he put forth, the principal inventor of the present invention discloses a fabrication process for a real three-dimensional micro channel structure, wherein it involves the lithographic technique of a thick film photoresist, forming a micro structure by controlling the exposure dosage of UV light, and thus cutting the manufacturing cost and simplifying the fabrication process. Hence, the proposed fabrication process is superior to the conventional fabrication process. In general, microfluidic devices are restricted by their fabrication method to such an extent that they have only two-dimensional micro channels, thus it is impossible to connect micro channels that belong to different networks in parallel. Hence, these microfluidic devices have their limitations, as far as the scope of their applications and their operating methods are concerned.

SUMMARY OF THE INVENTION

The first objective of the present invention is to provide a microfludic device with network micro channels, wherein a plurality of H-shaped micro channels divert a reagent into a predetermined location, so that its enzyme gets is placed accurately and its dosage is kept under control. The H-shaped micro channels can appear in the form of an open channel structure, or a polymer layer can be put on top of them to form a closed channel structure. Similarly, a multi-layer polymer structure can be stacked on the H-shaped micro channels.

The second objective of the present invention is to immobilize a reagent on a plurality of sub-channels that are parallel in longitudinal direction in light of the difference in the width of the micro channels, so that the reagent may not overflow into the next main channel that is perpendicular to and connected to the sub-channels to cause cross contamination.

The third objective of the present invention is to divert a reagent from a main channel to sub-channels that are perpendicularly connected to the main channel, then make the reagent flow into another main channel connected to the other end of the sub-channels. As a result, the flow of the fluid is always kept under control, so that the fluid can run at a constant speed or a variable speed.

The fourth objective of the present invention is to provide a biochip characterized by high throughput and fast sensing response. The micro channels of various networks on the biochip are separately filled with various reagents. Array-arrangement reactions of various samples and various reagents will take place whenever the samples to be tested are dropped into corresponding entrances of an upper layer.

In order to achieve these objectives, the present invention discloses a microfluidic device with network micro channels. A plurality of H-shaped micro channels not connected to each other are formed on a substrate. Each of the H-shaped micro channels comprises two main channels separately placed on two opposite sides in parallel and a plurality of sub-channels are perpendicularly connected to the two main channels. The present invention is designed in such a way that various reagents dropped into different H-shaped micro channels are immobilized on respective sub-channels because of the different widths of the main channel and sub-channel. Afterwards the reagents are coated with a layer of polymer. The polymer has a porous structure that allows the passage of any sample to be tested. Finally, a plurality of upper channels parallel to one another are directly fabricated in the polymer, or in another layer of polymer stacked on the previous polymer. Each of the upper channels is horizontally across and vertically through the space above respective sub-channels of the various H-shaped micro channels. In this way, various samples to be tested are respectively dropped into individual upper channels so that the samples will react with each of the reagents in the sub-channels.

BRIEF DESCRIPTION OF THE DRAWINGS

The invention will be described referring to the appended drawings in which.

PREFERRED EMBODIMENT OF THE PRESENT INVENTION

Figure 1A:
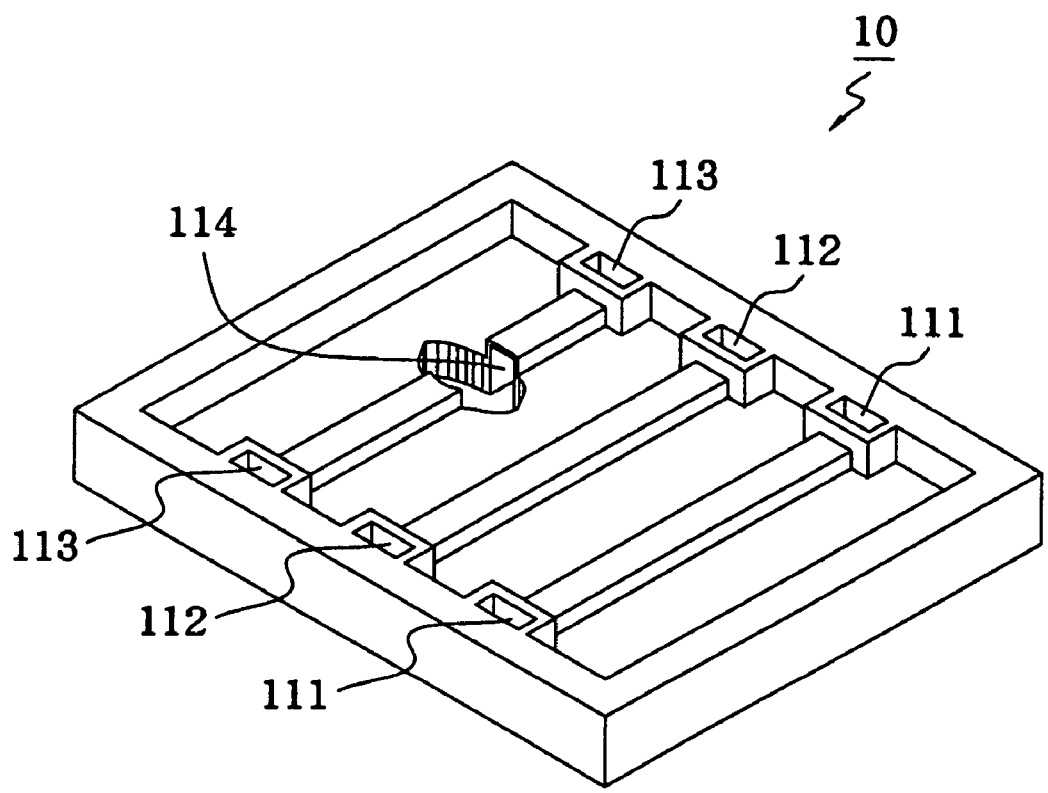
FIG. 1(a) is a perspective schematic diagram of the closed sample diversion layer of the microfluidic device in accordance with the present invention.
Figure 1B:
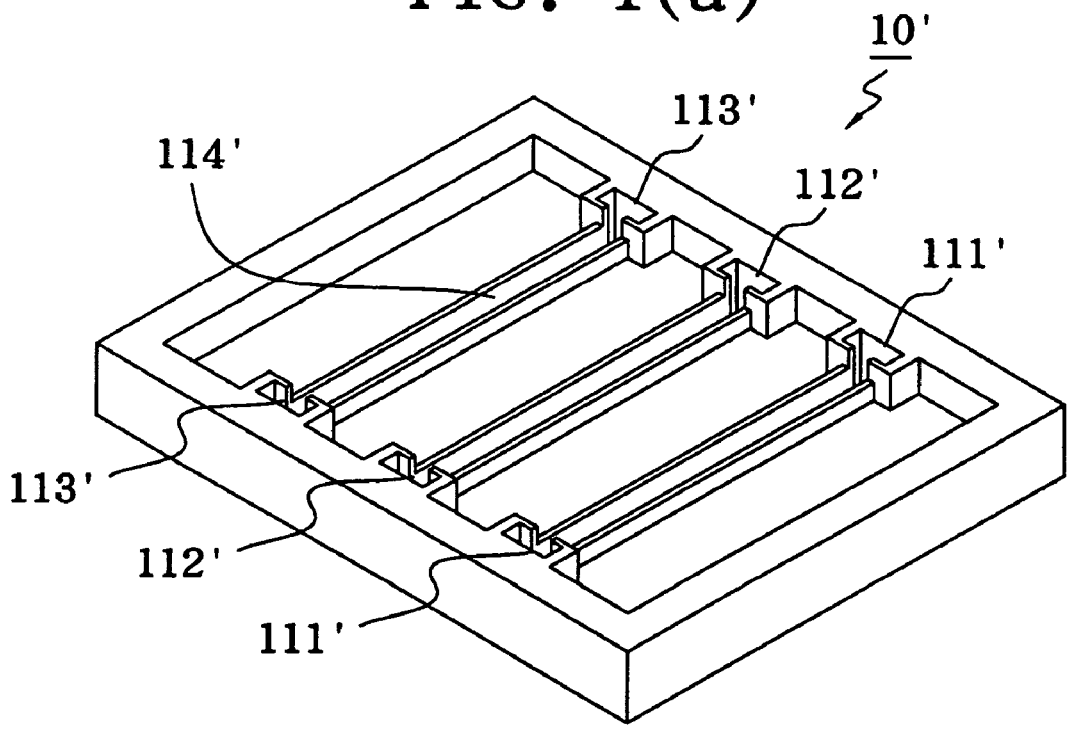
FIG. 1(b) is a perspective schematic diagram of the open sample diversion layer of the microfluidic device in accordance with the present invention.

FIG. 1(a) is a perspective schematic diagram of the closed sample diversion layer of the microfluidic device in accordance with the present invention. A sample diversion layer 10 made of polymer has both of its sides equipped with three sample dropping entrances 111, 112 and 113 each, allowing any samples to be tested to reach the channels inside. For instance, if a sample is dropped into the dropping entrance 111, the sample drops will pass through an embedded sample channel 114. Furthermore, it is also feasible to design an open sample diversion layer 10' as shown in FIG. 1(b), wherein each of the three sample dropping entrances 111', 112' and 113' has a sample channel 114' connected to it, and the sample channels 114' have become open channels in contrast with the embedded sample channel 114.

Figure 2:
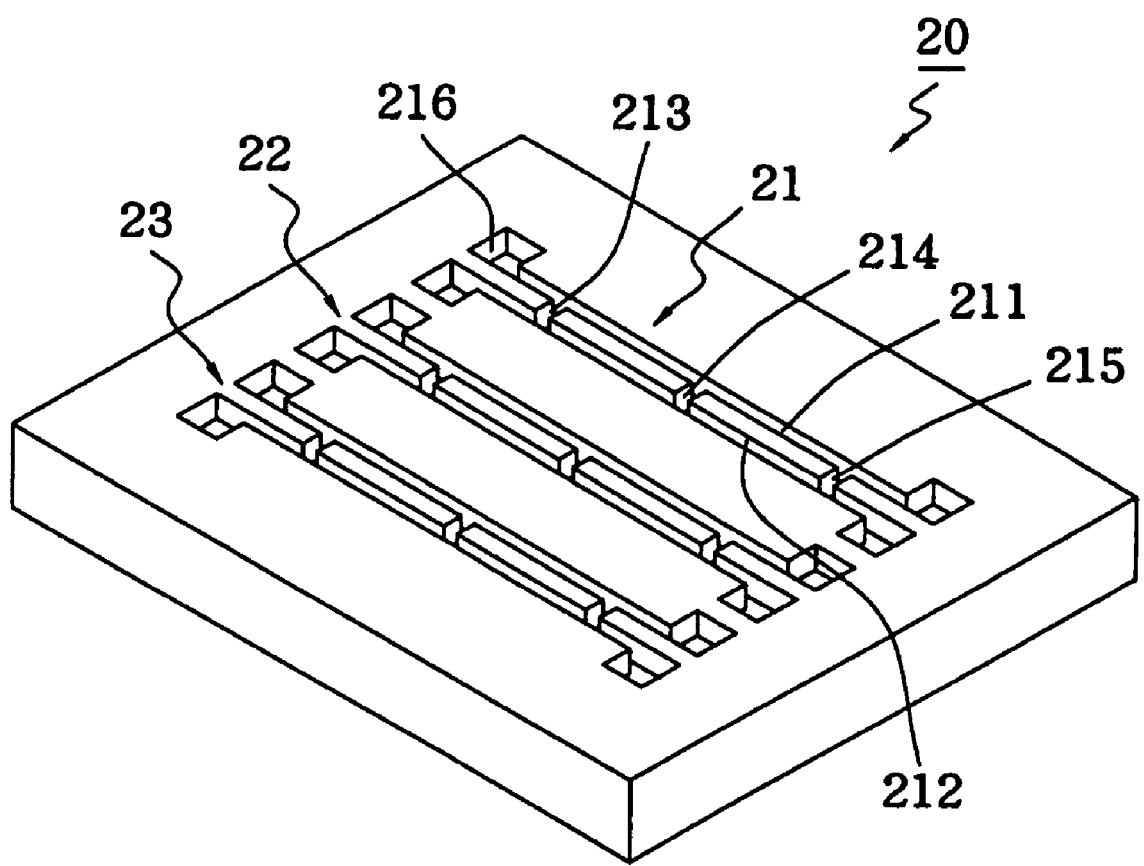
FIG. 2 is a perspective schematic diagram of the reagent immobilization layer of the microfluidic device in accordance with the present invention.
Figure 3:
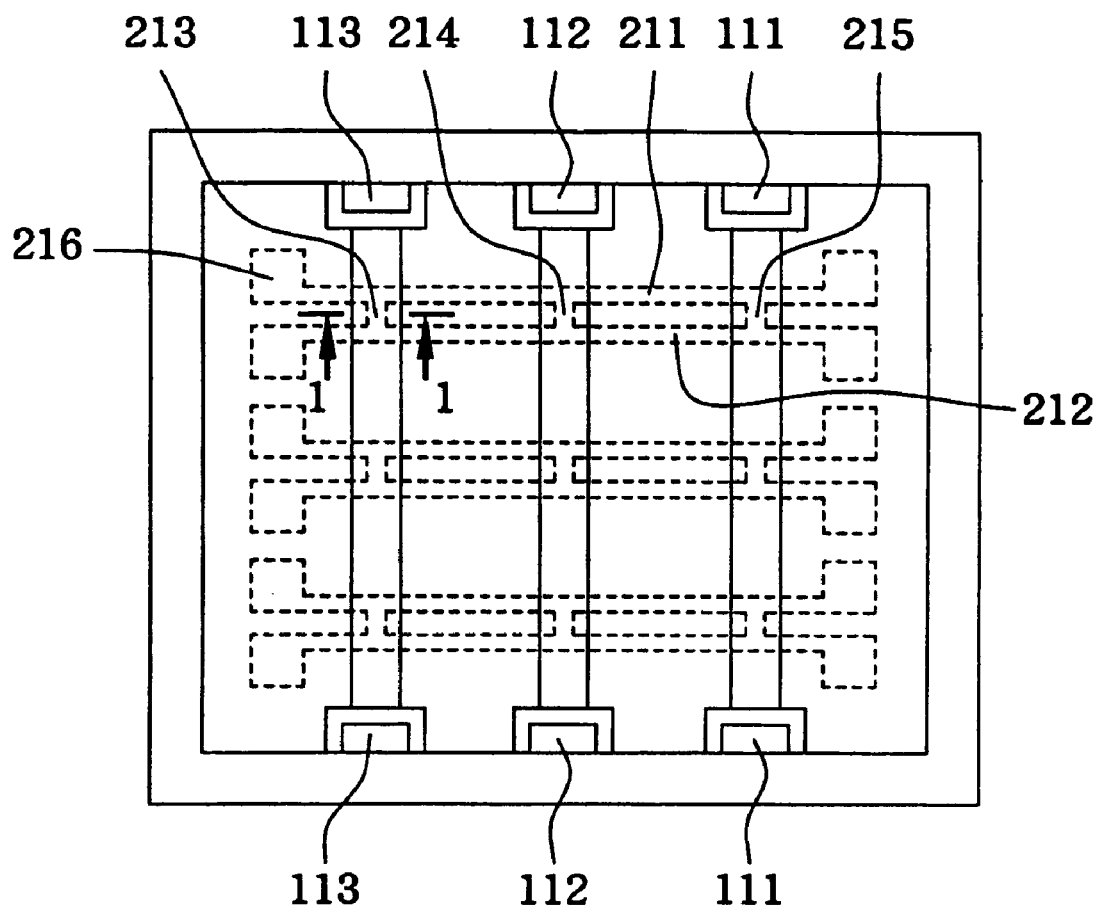
FIG. 3 is a top view of the microfluidic device in accordance with a preferred embodiment of the present invention.

In addition, a reagent immobilization layer 20 is provided underneath the sample diversion layer 10. Three independent, but similar, H-shaped micro channels 21, 22 and 23 are provided on the upper surface of the reagent immobilization layer 20, as shown in FIG. 2. The H-shaped micro channel 21 has two main channels 211 and 212 that are parallel to each other. Three sub-channels 213, 214 and 215 parallel to one another are perpendicularly formed between the main channels 211 and 212. Hence, all the channels are linked up. Each of the two ends of the main channels 211 and 212 is equipped with a reagent tank 216. A user may select a suitable position to drop a reagent into one of the reagent tanks 216, and then all the sub-channels 213, 214 and 215 are automatically filled with the reagent. The number of the H-shaped micro channels and the number of sub-channels are not restricted by the present embodiment; instead the layout may be designed to meet the actual demand. The microfluidic device with network micro channels (hereinafter referred to as the "microfluidic device") disclosed by the present invention is fabricated, by stacking the sample diversion layer 10 along with the reagent immobilization layer 20, as shown in FIG. 3.

Figure 4:
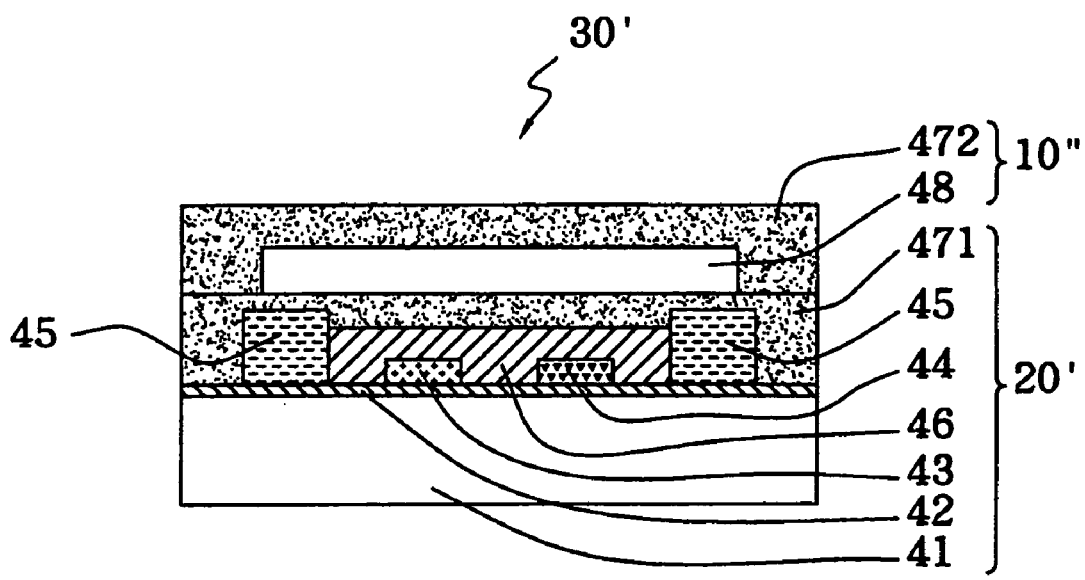
FIG. 4 is a schematic cross-section diagram along the line 1—1 in FIG. 3.
Figure 5A:
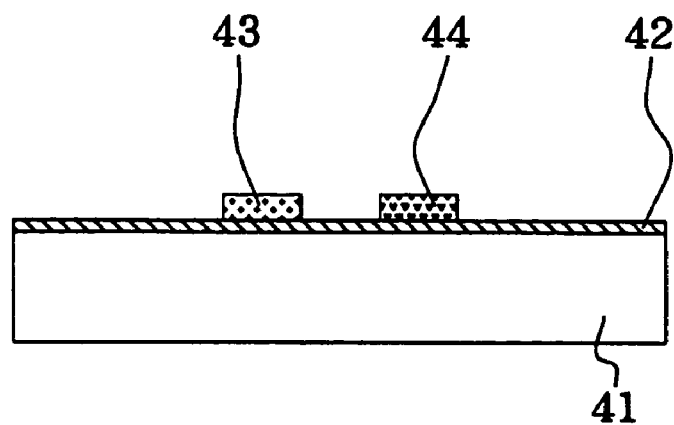
FIGS. 5(a)–5(e) are the schematic diagrams of the steps of the fabrication process in accordance with a preferred embodiment of the present invention.
Figure 5B:
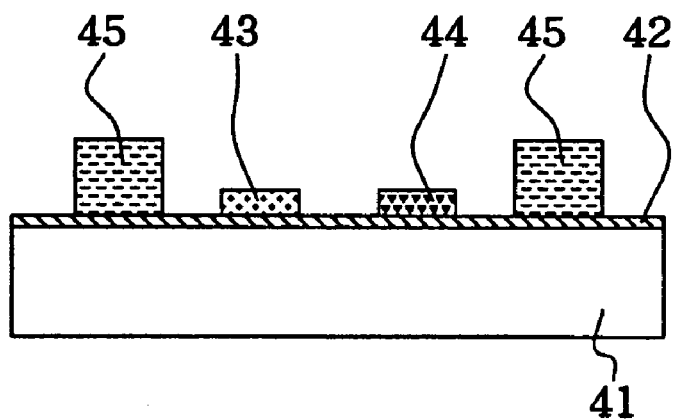
Figure 5C:
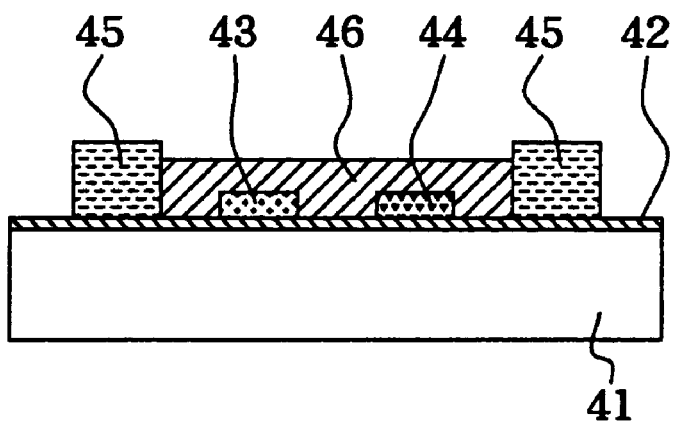
Figure 5D:
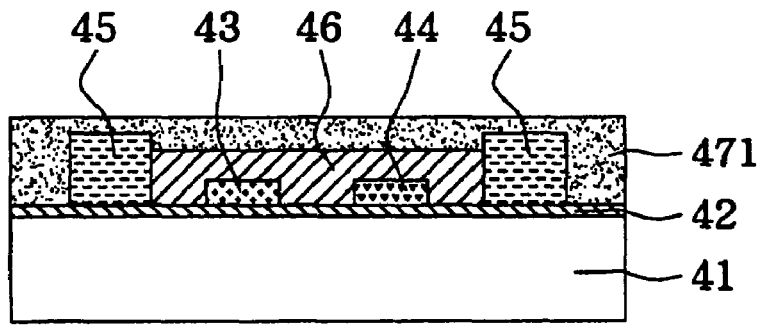
Figure 5E:
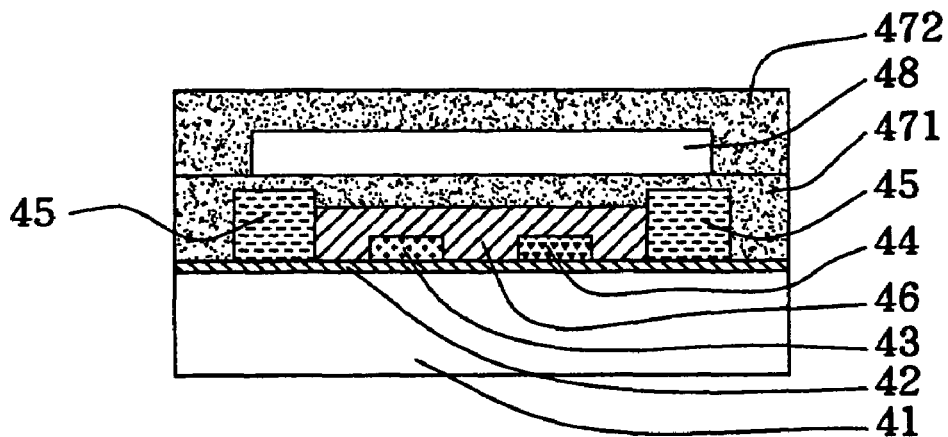

The microfluidic device 30' involves testing different samples with respective reagents suitable for them. FIG. 4 is a schematic cross-section diagram along the line 1—1 in FIG. 3. There it shows that a reagent, enzyme 46, is intended for the measurement of glucose concentration in blood, and for this reason it is also known as a glucose sensor. Blood enters and fills up the sample channel 48 via the sample dropping entrance 113. A PDMS layer 472 above the sample channel 48 guides the blood to the right places. The sample channel 48 and the PDMS layer 472 together form a closed sample diversion layer 10'. Glucose molecules in blood penetrate a PDMS layer 471 below, as the porous structure of the PDMS layer 471 allows the passage of glucose molecules. Once glucose molecules come into contact with the enzyme 46, oxidation will occur and products like glucuronic acid and hydrogen peroxide will be produced. At a working electrode 44 (which can be made from platinum or gold), hydrogen peroxide decomposes and releases electrons, and the electrons shift to a reference electrode (which can be made from silver). Meanwhile, an electric current is generated to function as an index of glucose concentration. On each of the two sides of the enzyme 46, a thick film photoresist 45 is erected, and is coupled with an underlying silica layer 42 to form a channel filled with the enzyme 46. A substrate 41 is beneath the silica layer 42. A reagent immobilization layer 20' is formed between the substrate 41 and the PDMS layer 471.

FIGS. 5(a)–5(e) are the schematic diagrams of the steps of the fabrication process in accordance with a preferred embodiment of the present invention. In the first place, a uniform silica layer 42 is formed on the substrate 41. Then, the working electrode 43 and the reference electrode 44 are molded above the silica layer 42 by means of deposition and etching, respectively. The walls of channels with high aspect ratio are built on the external sides of the two electrodes by means of the thick film photoresist 45 (preferably with SU-8). Hence, if drops of the enzyme 46 are dropped into one of the reagent tanks 216, they will automatically fill up each sub-channel due to the traction of surface tension and submerge the working electrode 43 and the reference electrode 44. It is recommended that the inner walls of the channels should be subjected to plasma processing beforehand so as to enhance the bonding between the channels and the enzyme 46. It is necessary to deposit a layer of polymer, preferably the PDMS layer 471, above the enzyme 46. At this point, the reagent immobilization layer 20' is fully formed. In addition, the space above the reagent immobilization layer 20' is covered with the same polymer to form the sample channel 48. In this way, the sample diversion layer 10' is also done. That is, the entire fabrication process of the glucose sensor 30' is finished.

Figure 6:
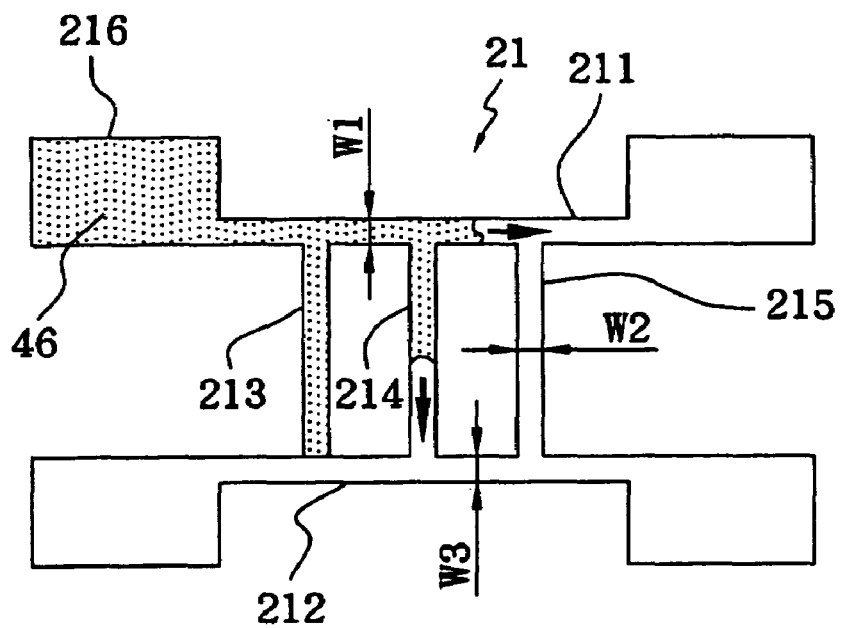
FIG. 6 is a schematic diagram of the corresponding dimensions of a H-shaped micro channel in accordance with a preferred embodiment of the present invention.

FIG. 6 is a schematic diagram of the corresponding dimensions of a H-shaped micro channel in accordance with a preferred embodiment of the present invention. The width of the main channel 211 is denoted by W1, whereas that of the main channel 212 is denoted by W3 and the widths of the sub-channels 213, 214 and 215 by W2, respectively. To satisfy the expression of the dimensional design W1=W3>W2, the enzyme 46 solution has to be diverted from the reagent tank 216 to the main channel 211 and flow into sub-channels 213, 214 and 215 through the respective intersections. Cross contamination is prevented, because of the dimensional effect under which the enzyme 46 solution fills each sub-channel, but never overflows into another main channel 211.

Figure 7:
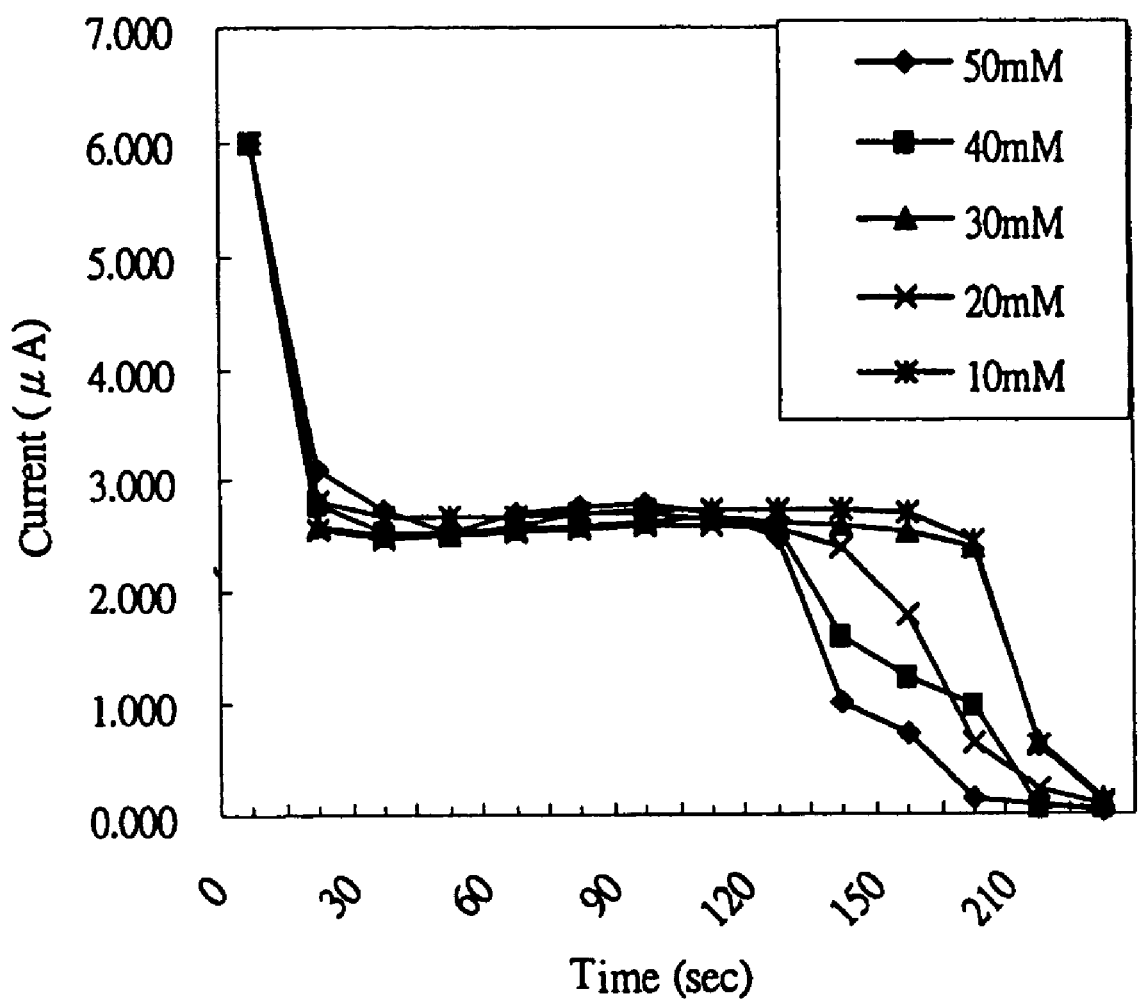
FIG. 7 shows the responses for the microfluidic device in accordance with a preferred embodiment of the present invention to samples to be tested.

Given the above-mentioned fabrication steps, it is feasible to fabricate the glucose sensor 30. FIG. 7 is a diagram that depicts its reactivity toward glucose concentration on the basis of the findings of a test conducted on it. The diagram indicates that the device proposed by the present invention is fit for detection of glucose concentration as low as 10 mM.

Figure 8A:
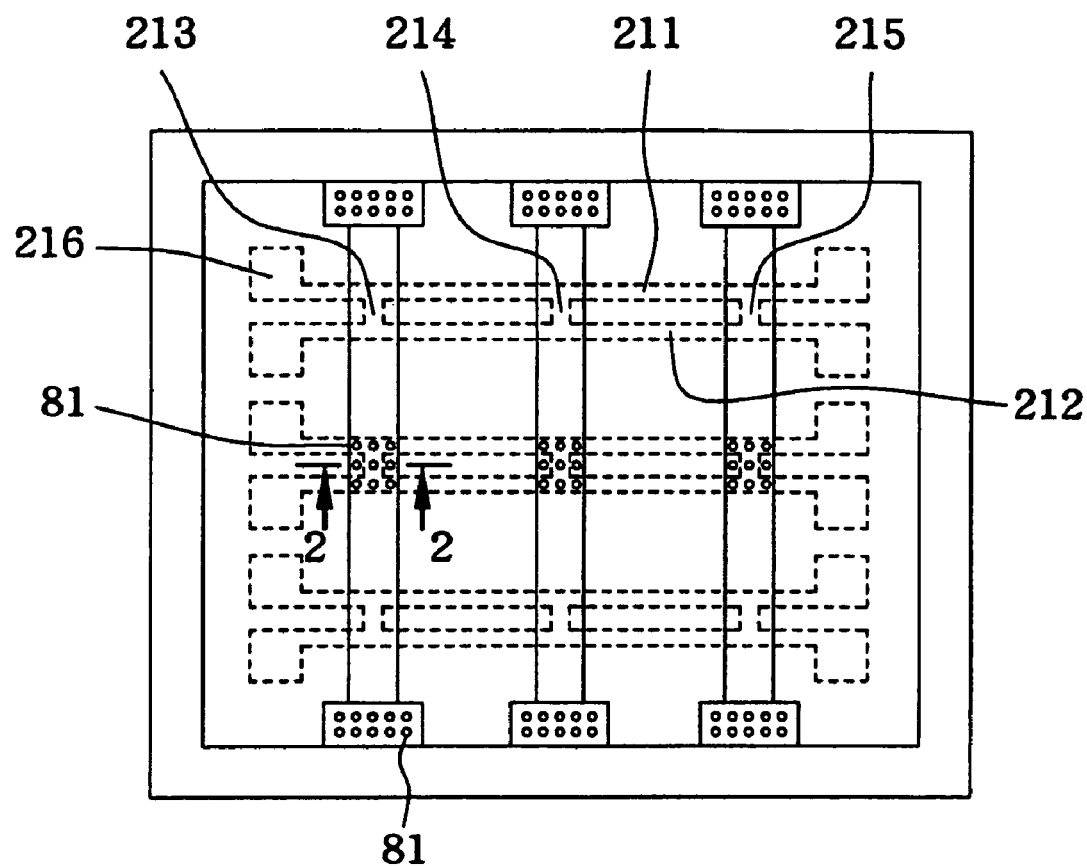
FIG. 8(a) is a top view of the microfluidic device in accordance with another preferred embodiment of the present invention.

FIG. 8(a) is a top view of the microfluidic device in accordance with another preferred embodiment of the present invention. In comparison with FIG. 3, we can replace the sample dropping entrance with a micro-needle array that comprises a plurality of miniature needles 81 arranged in a matrix. Each of miniature needles 81 or each of micro-needle arrays, like the needle of a syringe, can puncture human epidermis to draw blood or inject a drug.

Figure 8B:
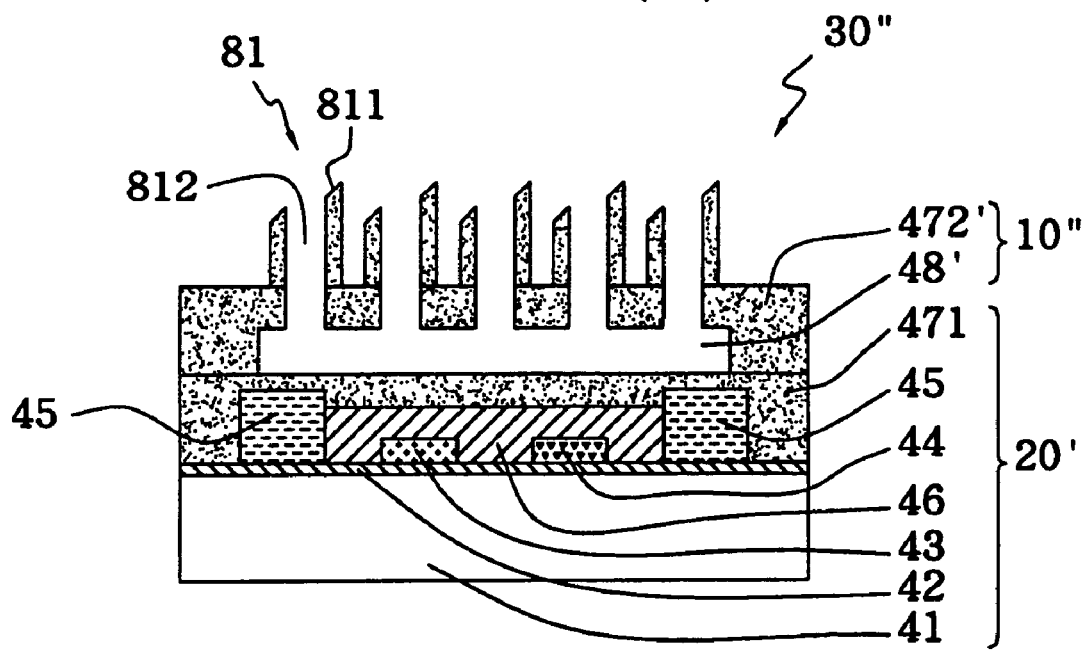
FIG. 8(b) is a schematic cross-section diagram along the line 2—2 in FIG. 8(a).

FIG. 8(b) is a schematic cross-section diagram along the line 2—2 in FIG. 8(a). The miniature needles 81 are formed on a sample diversion layer 10", and are integrated with a PDMS layer 472'. The through hole 812 of the miniature needle 81 is from the outside of the glucose sensor 30" to the sample channel 48'. It is recommended that the inner diameter of the through hole 812 should be from 10 µm to 500 µm to ensure blood samples are not damaged. A wall 811 surrounding the through hole 812 stands on the PDMS layer 472'. The miniature needle 81 with an inclined opening is easy to puncture human epidermis.

The above-described embodiments of the present invention are intended to be illustrative only. Numerous alternative embodiments may be devised by persons skilled in the art without departing from the scope of the following claims.

What is claimed is:

1. A microfluidic device with network micro channels, comprising:
   a substrate;
   at least two H-shaped micro channels formed on the substrate, each H-shaped micro channel including:
   (a) two main channels; and
   (b) at least one sub-channel, wherein two ends of the sub-channel are separately connected to the two main channels;
   a reagent filled in the at least one sub-channel; and
   a sample diversion layer having at least one sample channel with at least one sample entrance placed above the at least one sub-channel.

2. The microfluidic device with network micro channels of claim 1, wherein the widths of the two main channels are equal and the width of the main channel is larger than each width of the sub-channel.

3. The microfluidic device with network micro channels of claim 1, further comprising a working electrode and a reference electrode formed on a base of the sub-channel.

4. The microfluidic device with network micro channels of claim 3, wherein the material of the reference electrode is selected from platinum and gold.

5. The microfluidic device with network micro channels of claim 3, wherein the material of the working electrode is silver.

6. The microfluidic device with network micro channels of claim 1, further comprising a polymer material with porous structure coated on the reagent and the substrate.

7. The microfluidic device with network micro channels of claim 6, wherein the polymer material is a PDMS (polydimethylsiloxane) material.

8. The microfluidic device with network micro channels of claim 1, wherein the sample diversion layer is made of a polymer material.

9. The microfluidic device with network micro channels of claim 8, wherein the material of the polymer material is a PDMS material.

10. The microfluidic device with network micro channels of claim 1, wherein the main channel has at least one reagent tank.

11. The microfluidic device with network micro channels of claim 1, wherein the sidewalls of the main channel and the sub-channel are made from a thick film photoresist.

12. The microfluidic device with network micro channels of claim 11, wherein the thick film photoresist is a SU-8 photoresist.

13. The microfluidic device with network micro channels of claim 1, further comprising a silica layer formed on the substrate to be the base of the H-shaped micro channel.

14. The microfluidic device with network micro channels of claim 1, wherein the reagent is an enzyme.

15. The microfluidic device with network micro channels of claim 1, wherein the sample channel of the sample diversion layer is a closed channel.

16. The microfluidic device with network micro channels of claim 1, wherein the sample channel of the sample diversion layer is an open channel.

17. The microfluidic device with network micro channels of claim 1, wherein the sample entrance is a micro-needle array.

18. The microfluidic device with network micro channels of claim 17, wherein the micro-needle array has a plurality of miniature needles arranged in a matrix.

19. The microfluidic device with network micro channels of claim 18, wherein the inner diameter of each miniature needle is in a range of 10 μm to 500 μm.

* * * * *